(12) United States Patent
Teshima et al.

(10) Patent No.: US 11,746,099 B2
(45) Date of Patent: *Sep. 5, 2023

(54) METHOD FOR PRODUCING OPTICALLY ACTIVE PYRROLIDINE COMPOUNDS

(71) Applicant: MITSUBISHI TANABE PHARMA CORPORATION, Osaka (JP)

(72) Inventors: Takao Teshima, Osaka (JP); Takafumi Yamagami, Osaka (JP); Tetsuo Yamaguchi, Osaka (JP); Junki Ando, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/344,152

(22) Filed: Jun. 10, 2021

(65) Prior Publication Data

US 2021/0300896 A1 Sep. 30, 2021
US 2022/0119364 A2 Apr. 21, 2022

Related U.S. Application Data

(63) Continuation of application No. 16/481,690, filed as application No. PCT/JP2018/002878 on Jan. 30, 2018, now Pat. No. 11,104,662.

(30) Foreign Application Priority Data

Jan. 31, 2017 (JP) .................. 2017-014999

(51) Int. Cl.
*C07D 401/10* (2006.01)
*C07B 53/00* (2006.01)
*C07D 207/09* (2006.01)
*C07D 211/62* (2006.01)

(52) U.S. Cl.
CPC ............ *C07D 401/10* (2013.01); *C07B 53/00* (2013.01); *C07B 2200/07* (2013.01); *C07D 207/09* (2013.01); *C07D 211/62* (2013.01)

(58) Field of Classification Search
CPC .. C07D 401/10; C07D 207/09; C07D 211/62; C07B 53/00; C07B 2200/07
See application file for complete search history.

(56) References Cited

U.S. PATENT DOCUMENTS 9,981,960 B2 * 5/2018 Yamamoto ............ C07D 401/10
11,104,662 B2 * 8/2021 Teshima ............... C07D 401/10
2009/0137819 A1 5/2009 Yasuoka et al.
2017/0190697 A1 7/2017 Yamamoto et al.

FOREIGN PATENT DOCUMENTS

WO WO 2007/066828 A1 6/2007
WO WO 2015/182723 A1 12/2015

OTHER PUBLICATIONS

Berge, 1977, J Pharm Sciences, vol. 66(1), 1-19. (Year: 1977).*

(Continued)

*Primary Examiner* — D Margaret M Seaman
(74) *Attorney, Agent, or Firm* — Birch, Stewart, Kolasch & Birch, LLP

(57) ABSTRACT

The present invention provides a process for preparing a compound represented by formula (VII), which comprises reacting a compound represented by formula (VI) with a malonic acid derivative in the presence of a base and an asymmetric catalyst in a two layer solvent system of hydrophobic solvent and water,

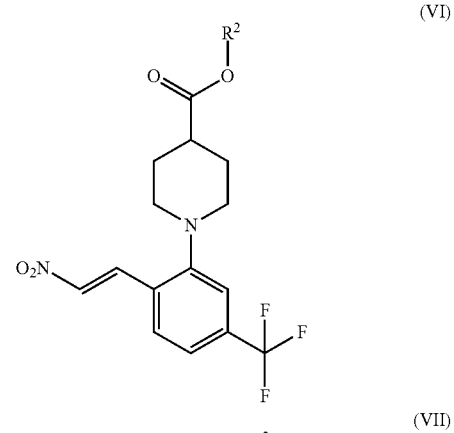

(VI)

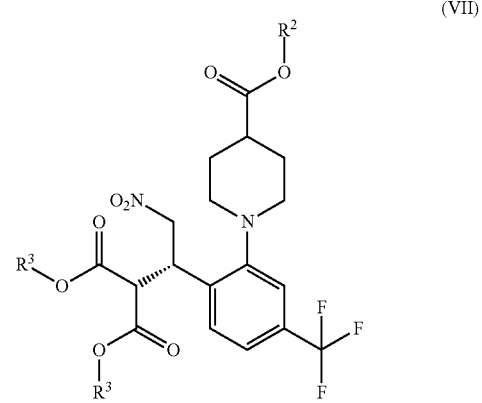

(VII)

(wherein $R^2$ and $R^3$ each independently represents a protecting group for carboxyl group).

1 Claim, No Drawings

(56) References Cited

OTHER PUBLICATIONS

Almasi et al., "Chiral 2-Aminobenzimidazoles as Recoverable Organocatalysts for the Addition of 1,3-Dicarbonyl Compounds to Nitroalkenes", Journal of Organic Chemistry, 2009, vol. 74, No. 16, pp. 6163-6168.
Berge, S.M., et al, "Pharmaceutical Salts," Journal of Pharmaceutical Sciences, Jan. 1977, vol. 66, No. 1, pp. 1-19.
Chen et al., "Asymmetric Michael Addition of Trisubstituted Carbanion to Nitroalkenes Catalyzed by Sodium Demethylquinine Sait in Water", Chirality, 2009, vol. 21, No. 6, pp. 600-603.
Extended European Search Report dated Jul. 8, 2020, in European Patent Application No. 18747316.0.
International Preliminary Report on Patentability and English translation of the Written Opinion of the International Searching Authority for International Application No. PCT/JP2018/002878, dated Aug. 15, 2019.
International Search Report for International Application No. PCT/JP2018/002878 dated Mar. 13, 2018.

* cited by examiner

METHOD FOR PRODUCING OPTICALLY ACTIVE PYRROLIDINE COMPOUNDS

This application is a Continuation of copending application Ser. No. 16/481,690 filed on Jul. 31, 2019, which is the U.S. National Phase of PCT/JP2018/002878, filed Jan. 30, 2018, and which claims priority under 35 U.S.C. § 119(a) to Application No. 2017-014999 filed in Japan, on Jan. 31, 2017, the entire contents of all of which are expressly incorporated by reference into the present application.

TECHNICAL FIELD

The present invention is related to a novel process for preparing optically active pyrrolidine compounds which are useful as synthetic intermediate compounds for drug substances.

BACKGROUND ART

The optically active pyrrolidine compound is a compound having optically active substituents on 3-position and 4-position in the pyrrolidine ring, and is useful as a synthetic intermediate compound for drug substance. As a process for preparing the optically active pyrrolidine compound, for example, the patent document 1 discloses that nitromethane is reacted with a benzaldehyde derivative, and the obtained nitrostylene derivative is subjected to an additive reaction of malonic acid diester, followed by cyclization of the reaction intermediate compound (see page 330, Reference Example 112 and son on). Here in all the steps, a reaction is conducted in a single layer solvent system of organic solvent which is different from a solvent that is used in a pre-step to the given step, and also in all the steps, isolating procedures such as purification and drying are conducted.

Also, the Patent document 2 discloses that nitromethane is reacted with benzaldehyde to obtain hydrous crystals of nitrostylene, and the crystals are dehydrated in situ, which are thereafter subjected to an additive reaction of malonic acid diester in an organic solvent, followed by reduction reaction and cyclization reaction of the reaction intermediate compound. Here the reaction of nitrostylene with malonic acid diester is conducted in monophasic organic solvent after removing water contained in nitrostylene crystals by working up such as a separation procedure with a separatory funnel, or an azeotropic procedure.

Accordingly, a process for subjecting nitrostylene or derivatives thereof without obtaining as a crystal to an additive reaction of a malonic acid derivative has not been known yet.

Also, generally, nitro compounds such as nitrostylene derivatives have some risks of explosion. Especially in an industrial production in which a large amount of compounds are treated, nitro compounds are thus said to be compounds to be avoided from obtaining them as a crystal or performing worked up procedures such as drying.

CITATION LIST

Patent Document

Patent Document 1: WO 2015/182723
Patent Document 2: WO 2007/066828

SUMMARY OF THE INVENTION

Problems to be Solved by Invention

For an additive reaction of malonic acid derivative to a certain nitrostylene derivative, a known reaction in a single layer solvent system of organic solvent sometimes cannot provide sufficient reaction rates, reaction yields, and enantioselectivity. Also, when any solvent containing water is used in a pre-step of the additive reaction, in order to conduct the reaction in organic solvent(s), it is required to obtain a nitrostylene derivative having some risks of explosion as a crystal to be used as a starting material, and also to remove moisture strictly. Accordingly, it has been desired to develop a high-yield, industrially advantageous and safe process for additive reaction of a malonic acid derivative to a nitrostylene derivative.

Further, the optically active pyrrolidine compound which is useful as a synthetic intermediate compound for drug substance requires multiple steps to prepare it due to a complexity of its structure, and in the process in which the purification and/or drying is/are conducted in each step, there has been some problems in manufacturing costs.

Thus the purpose of the present invention is to provide a process for preparing an optically active pyrrolidine compound which is suitable for an industrial production that solves these problems.

Means to Solve Problems

The present inventors have variously studied to conduct each process safely and reproducibly in high yield, and as a result, found out that in an additive reaction of malonic acid derivative to nitrostylene derivatives, since the nitrostylene derivatives were used in the unpurified state, an acidic substance derived from the pre-step reaction affects the reaction adversely, and accordingly established a process in which the present reaction is conducted in a two layer solvent system of a hydrophobic solvent and water in the presence of a base. The findings not only has realized an improvement in a reaction yield and an enantioselectivity of the additive reaction of a malonic acid derivative to a nitrostylene derivative, but also has eliminated the need to obtain the nitrostylene derivative having some risks of explosion as a crystal or to dry it because the presence of water in the reaction system has no adverse effect on the reaction, and has thus improved the safety of the reaction. Also, the present inventors have found out a process in which five steps reactions as described herein can be conducted successively while maintaining or improving a reaction yield, an enantioselectivity, an ease of operation, etc., of each step, and completed the invention of the present application.

That is, the present invention includes the followings [1] to [15], however, which are not limited thereto.

[1] A process for preparing a compound represented by formula (VII):

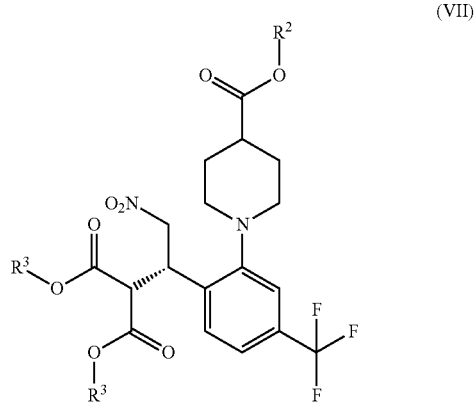

(VII)

(wherein R² and R³ each independently represents a protecting group for carboxyl group),
which comprises reacting a compound represented by formula (VI):

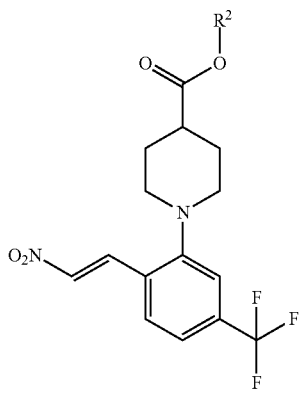

(VI)

(wherein R² represents a protecting group for carboxyl group) with a malonic acid derivative in the presence of a base and an asymmetric catalyst in a two layer solvent system of hydrophobic solvent and water.

[2] The process described in [1], which comprises reacting a compound represented by formula (V):

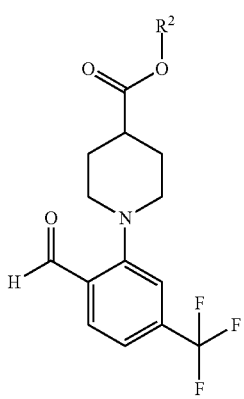

(V)

(wherein R² represents a protecting group for carboxyl group) with a nitromethane in the presence of a base to prepare a compound represented by formula (VI):

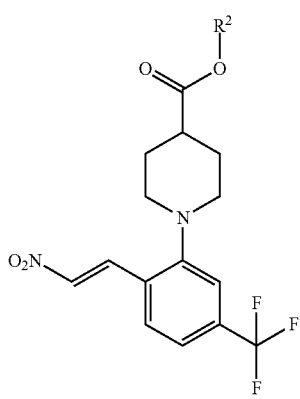

(VI)

(wherein R² represents a protecting group for carboxyl group), and
the resulting compound is then applied to a process described in [1] as a starting material without obtaining it as a crystal or drying it.

[2-1] The process described in [1], which comprises a compound represented by formula (V):

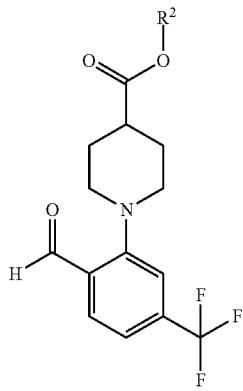

(V)

(wherein R² represents a protecting group for carboxyl group) with nitromethane in the presence of a base to prepare a compound represented by formula (VI):

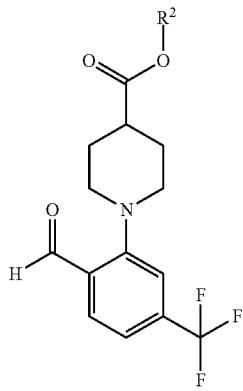

(VI)

(wherein R² represents a protecting group for carboxyl group), and
the compound is then applied to a process described in [1] as a starting material without obtaining it as a crystal and drying it.

[2-2] The process described in [2] or [2-1], which comprises reacting in the presence of at least one compounds selected from an optionally substituted alkyl sulfonyl halide, an optionally substituted aryl sulfonyl halide, and an optionally substituted alkyl halide.

[3] The process described in [2], which comprises conducting a step for preparing the compound represented by formula (VI) from the compound represented by formula (V) in a hydrophobic solvent, wherein the hydrophobic solvent is the same hydrophobic solvent that is used in the step for preparing the compound represented by formula (VII) from the compound represented by formula (VI).

[4] The process described in [2], which comprises reacting a compound represented by formula (III):

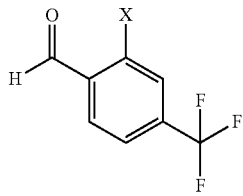
(III)

(wherein X represents a halogen atom, an optionally substituted alkyl sulfonyloxy group, or an optionally substituted aryl sulfonyloxy group.)
with a compound represented by formula (IV):

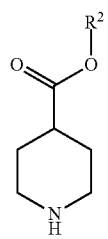
(IV)

(wherein $R^2$ represents a protecting group for carboxyl group) to prepare a compound represented by formula (V):

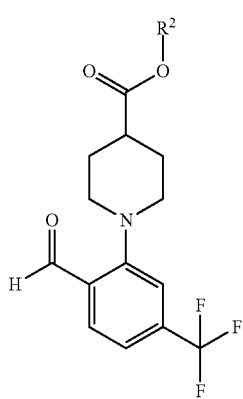
(V)

(wherein $R^2$ represents a protecting group for carboxyl group),
and the compound represented by formula (V) is then applied to a process described in [2] as a starting material without isolating it.
[5] The process described in [4], which comprises conducting the step for preparing the compound represented by formula (V) from the compound represented by formula (III) and the step for preparing the compound represented by formula (VI) from the compound represented by formula (V) in a hydrophobic solvent, wherein the hydrophobic solvent is the same solvent that is used in the step for preparing the compound represented by formula (VII) from the compound represented by formula (VI).
[6] The process described in [4], which comprises conducting a step for preparing the compound represented by formula (V) from the compound represented by formula (III) in a two layer solvent system of the hydrophobic solvent and water, and comprises conducting a step for preparing the compound represented by formula (VI) from the compound represented by formula (V) in a hydrophobic solvent, wherein the hydrophobic solvent that is used in these steps is the same hydrophobic solvents that is used in a step for preparing a compound represented by formula (VII) from a compound represented by formula (VI).
[7] A process for preparing a compound represented by formula (VIII):

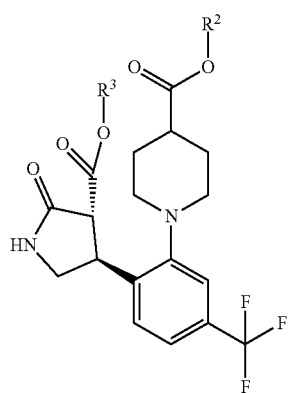
(VIII)

(wherein $R^2$ and $R^3$ each independently represents a protecting group for carboxyl group),
which comprises subjecting the compound represented by formula (VII) which is prepared by the process described in any one of [1] to [6] as a starting material to a ring closure reaction in the presence of a reducing agent.
[8] The process described in [7], which comprises applying as a starting material the compound represented by formula (VII) without isolating it to the process described in [7].
[9] The process described in [7], which comprises obtaining the compound represented by formula (VII) as a crystal and then applying the compound to the process described in [7].
[10] A process for preparing a compound represented by formula (IX):

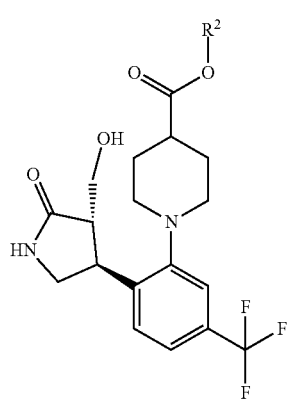
(IX)

(wherein $R^2$ represents a protecting group for carboxyl group), which comprises subjecting the compound represented by formula (VIII) which is prepared by the process described in any one of [7] to [9] as a starting material without isolating it to a reduction reaction.

[11] The process described in [10], wherein the step for preparing the compound represented by formula (VIII) from the compound represented by formula (VII), and the step for preparing the compound represented by formula (IX) from the compound represented by formula (VIII) are conducted in the same solvent.

[12] A process for preparing a compound represented by formula (II):

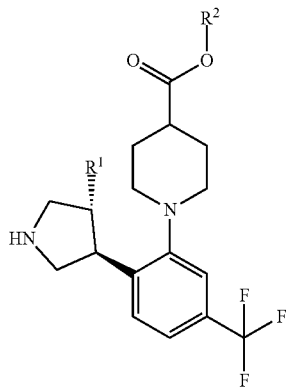

(II)

(wherein $R^1$ represents an alkyl group optionally substituted with one or more groups independently selected from a group consisting of halogen atom, hydroxyl group, cyano group and alkoxy group, and $R^2$ represents a protecting group for carboxyl group)
or a salt thereof,
which comprises converting the compound represented by formula (IX) which is prepared by a process described in [10] or [11] according to a known method, and further, if desired, making the resulting compound into a salt thereof.

[13] The process described in [12], wherein $R^1$ represents a methyl group optionally substituted with one or more groups independently selected from the group consisting of halogen atom, cyano group, and alkoxy group.

[14] A process for preparing a compound represented by formula (I):

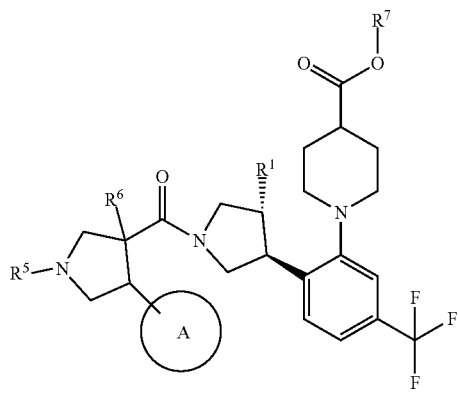

(I)

(wherein a ring A, $R^5$ and $R^6$ are the same as defined below, $R^1$ represents an alkyl group optionally substituted with one or more groups independently selected from the group consisting of halogen atom, hydroxyl group, cyano group and alkoxy group, and $R^7$ represents a hydrogen atom, or a protecting group for carboxyl group)
or a pharmaceutically acceptable salt thereof,
which comprises reacting the compound represented by formula (II) or a salt thereof which is prepared by the process described in [12] with a compound represented by formula (X):

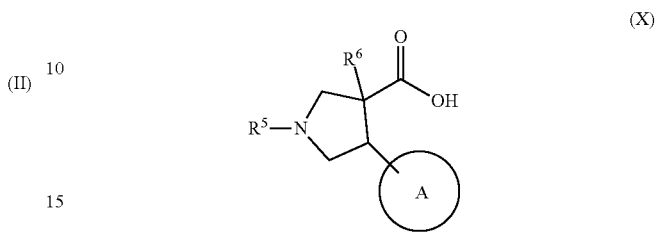

(X)

(wherein the ring A represents an optionally substituted aryl group, or an optionally substituted heteroaryl group, $R^5$ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, an optionally substituted carbamoyl group or a hydrogen atom, and $R^6$ represents a halogen atom, an alkyl group or an optionally substituted alkoxy group) or a salt thereof according to a known method, and further, if desired, making the resulting compound into a pharmaceutically acceptable salt thereof.

[15] A process for preparing a compound represented by formula (I):

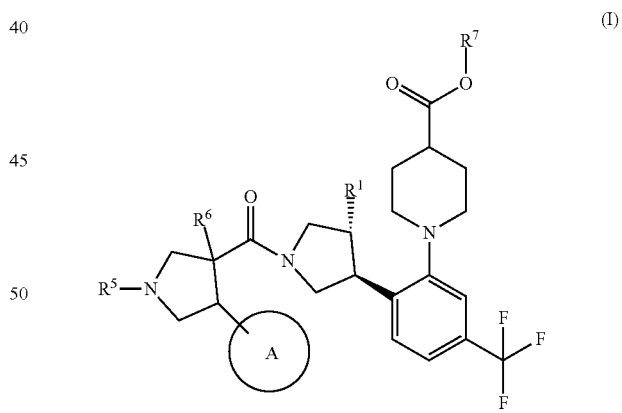

(I)

(wherein the ring A, $R^5$, and $R^6$ are the same as defined below, $R^1$ represents a methyl group optionally substituted with one or more groups independently selected from the group consisting of halogen atom, cyano group and alkoxy group, and $R^7$ represents a hydrogen atom or a protecting group for carboxyl group), or a pharmaceutically acceptable salt thereof,
which comprises reacting the compound represented by formula (II) which is prepared by the process described in [13] or a salt thereof with a compound represented by formula (X):

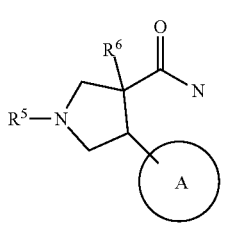

(X)

(wherein the ring A represents an optionally substituted aryl group, or an optionally substituted heteroaryl group, $R^5$ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, an optionally substituted carbamoyl group, or a hydrogen atom, and $R^6$ represents a halogen atom, an alkyl group, or an optionally substituted alkoxy group) or a salt thereof, According to a known method, and further, if desired, making the resulting compound into a pharmaceutically acceptable salt thereof.

[16] A salt represented by formula (XI):

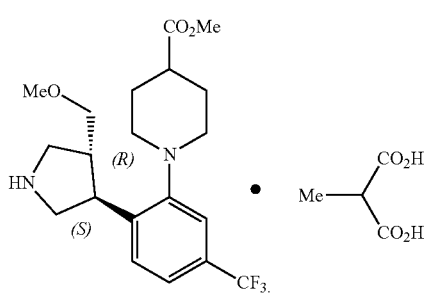

(XI)

[17] The process described in any one of [12] or [13] wherein the salt of the compound represented by formula (II) is the salt represented by formula (XI) which is described in [16].

[18] The process described in any one of [14] or [15] wherein the salt of the compound represented by formula (II) is the salt represented by formula (XI) which is described in [16], and $R^1$ represents a methoxymethyl group in the compound represented by formula (I).

Effect of Invention

According to the present invention, an additive reaction of a malonic acid derivative to a nitrostylene derivative can be conducted in high yield and with high enantioselectivity without decreasing a reaction rate. Also, as described herein, three steps of reaction including the step for the above-described additive reaction can be conducted in the same solvent, and can avoid obtaining an intermediate compound having some risks of explosion as a crystal, and drying it. Further, according to the present invention, five steps of reaction including the above three steps can be conducted efficiently and successively, which can prepare an optically active pyrrolidine compound, which is useful as an intermediate compound for drug substance, in industrially advantageous manner.

According to the process of the present invention, the reproducibility and yields for each step are good, and also since the isolation of the product is not needed in each step, it is an advantageous production method in terms of a manufacturing cost.

MODE FOR CARRYING OUT THE INVENTION

The present invention relates to the following process.

(1) A process for preparing a compound represented by formula (VII):

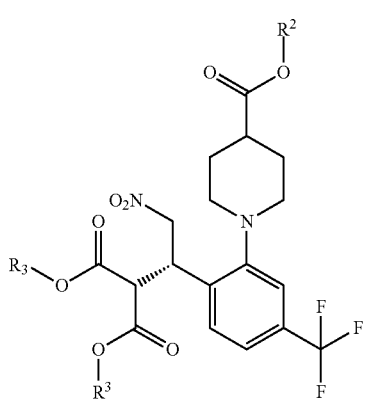

(VII)

(wherein $R^2$ and $R^3$ each independently represents a protecting group for carboxyl group),
which comprises reacting a compound represented by formula (VI):

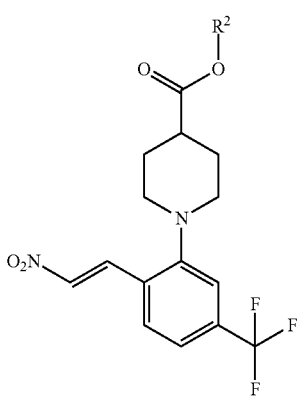

(VI)

(wherein $R^2$ represents a protecting group for carboxyl group) with a malonic acid derivative in the presence of a base and an asymmetric catalyst in a two layer solvent system of hydrophobic solvent and water.

(2) The process for preparing a compound represented by formula (VII), which comprises reacting a compound represented by formula (V):

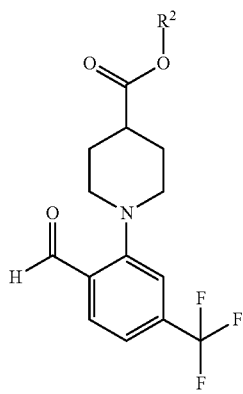

(V)

(wherein R² represents a protecting group for carboxyl group) with a nitromethane in the presence of a base to prepare a compound represented by formula (VI):

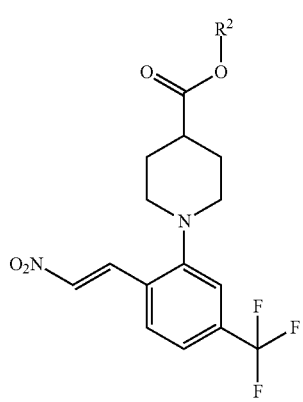

(VI)

(wherein R² represents a protecting group for carboxyl group), and the resulting compound is then applied to a process described in the above-described (1) as a starting material without obtaining it as a crystal and/or drying it.

(3) The process for preparing a compound represented by formula (VII), which comprises reacting a compound represented by formula (III):

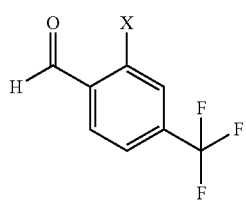

(III)

(wherein X represents a halogen atom, an optionally substituted alkyl sulfonyloxy group, or an optionally substituted aryl sulfonyloxy group) with a compound represented by formula (IV):

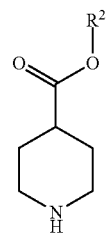

(IV)

(wherein R² represents a protecting group for carboxyl group) or a salt thereof
to prepare a compound represented by formula (V):

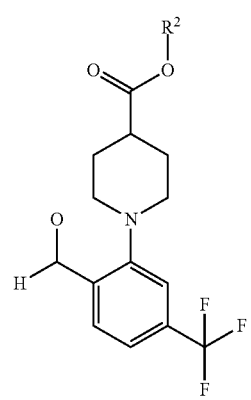

(V)

(wherein R² represents a protecting group for carboxyl group), and the resulting compound is then applied to a process described in the above-described (2) as a starting material without isolating it.

(4) A process for preparing a compound represented by formula (VIII):

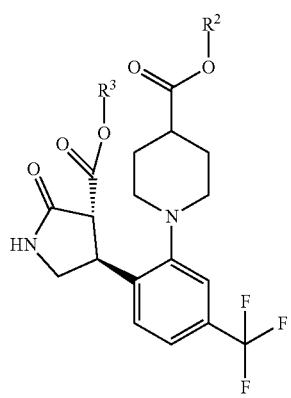

(VIII)

(wherein R² and R³ each independently represents a protecting group for carboxyl group),
which comprises obtaining the compound represented by formula (VII) which is prepared by the process described in any one of the above-described (1) to (3) without isolating it or as a crystal, and then subjecting the resulting compound as a starting material to a ring closure reaction by reduction in the presence of a reducing agent.

(5) A process for preparing a compound represented by formula (IX):

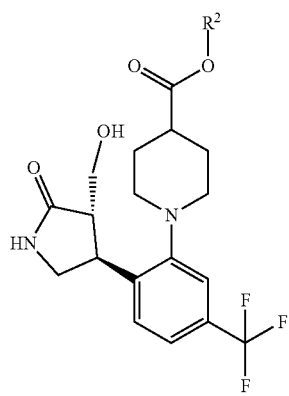

(wherein R² represents a protecting group for carboxyl group), which comprises subjecting the compound represented by formula (VIII) which is prepared by the process described in the above-described (4) as a starting material without isolating it, to a reduction reaction.

(6) A process for preparing a compound represented by formula (II):

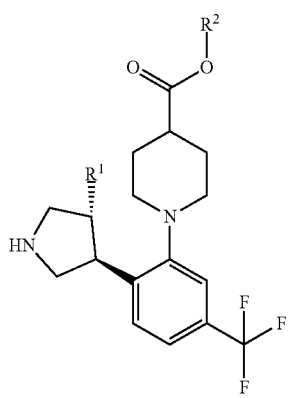

(wherein R¹ represents an alkyl group (such as methyl) optionally substituted with one or more groups independently selected from the group consisting of halogen atom, hydroxyl group, cyano group and alkoxy group, and R² represents a protecting group for carboxyl group)

or salts thereof, which comprises converting the compound represented by formula (IX) which is prepared by a process described in the above-described (5) according to a known method, and further, if desired, making the resulting compound into the salts thereof.

(7) A process for preparing a compound represented by formula (I):

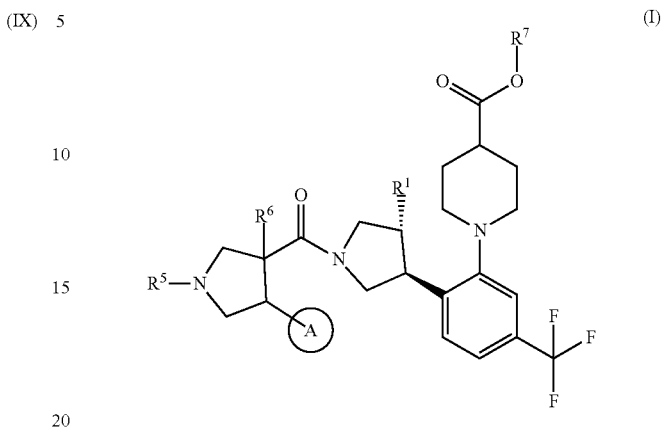

(wherein the ring A represents an optionally substituted aryl group, or an optionally substituted heteroaryl group, R¹ represents an alkyl group (such as methyl) optionally substituted with one or more groups independently selected from the group consisting of halogen atom, hydroxyl group, cyano group and alkoxy group, R⁵ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, an optionally substituted carbamoyl group, or a hydrogen atom, R⁶ represents a halogen atom, an alkyl group or an optionally substituted alkoxy group, and R⁷ represents a hydrogen atom, or a protecting group for carboxyl group)

or pharmaceutically acceptable salts thereof, which comprises converting the compound represented by formula (II) or salts thereof which is prepared by the process described in the above-described (6) according to a known method, and further, if desired, making the resulting compound into pharmaceutically acceptable salts thereof.

The definition of each group described herein can be combined as desired, unless otherwise specified.

As used herein, the "alkyl group" refers to a straight or branched saturated hydrocarbon chain group having one to six carbon atom(s) ($C_{1-6}$). Alkyl group having one to four carbon atom(s) ($C_{1-4}$) is particularly preferable. Specific examples thereof include methyl, ethyl, n-propyl, i-propyl, n-butyl, t-butyl, 2-methyl-n-butyl, i-amyl (3-methyl-n-butyl), and 2-methyl-n-pentyl. Methyl, ethyl, i-propyl, or t-butyl is particularly preferable.

As used herein, the substituent in "alkyl group optionally substituted with one or more groups independently selected from the group consisting of halogen atom, hydroxyl group, cyano group, and alkoxy group" includes one or more (for example, preferably one to three, or more preferably one to two) groups independently selected from the group consisting of halogen atom (such as chlorine atom, bromine atom, or iodine atom), hydroxyl group, cyano group, and alkoxy group (such as methoxy, ethoxy, n-propoxy, or i-propoxy), which are the identical to or different from each other. Preferred examples of the substituent include hydroxyl group or alkoxy group, and more preferred examples of the substituent include hydroxyl group, methoxy group, ethoxy group, and the others. Also, examples of the optionally substituted alkyl group include chloromethyl, chloroethyl, 1-chloroethyl, 1-bromoethyl, hydroxymethyl, 1-hydroxyethyl, methoxymethyl, 1-methoxyethyl, ethoxymethyl, 1-ethoxyethyl, and the others.

As used herein, the "alkenyl group" refers to a straight or branched saturated hydrocarbon chain group having 2 to 6 carbon atom(s) ($C_{2-6}$) and at least one double bond. Alkenyl group having two to four carbon atom(s) ($C_{2-4}$) is particularly preferable. Specific examples thereof include vinyl, propenyl (allyl), or butenyl.

As used herein, the alkoxy group" refers to a monovalent group in which the above-described alkyl group is attached to an oxygen atom, for example, a straight or branched alky-O— having one to six carbon atom(s) ($C_{1-6}$), and alky-O-having one to four carbon atom(s) ($C_{1-4}$) is preferable. Specific examples thereof include methoxy, ethoxy, n-propoxy, i-propoxy, n-butoxy, t-butoxy, 2-methyl-n-propoxy, 3-methyl-n-butoxy and the others. Methoxy, ethoxy, i-propoxy, and t-butoxy and the others are particularly preferable.

As used herein, the "alkanoyl group" refers to a group in which a carbonyl group (C=O) is attached to the above-described alkyl group, and includes a straight or branched alkyl-C(=O) group having one to six carbon atom(s) ($C_{1-6}$), and alkyl-C(=O) group having one to four carbon atom(s) is preferable. Specific examples thereof include acetyl, propionyl, butyryl and the others.

As used herein, the "alkylene group" refers to a straight or branched saturated hydrocarbon divalent group having one to six carbon atom(s) ($C_{1-6}$), and alkylene group having one to four carbon atom(s) ($C_{1-4}$) is preferable. Specific examples thereof includes methylene, ethylene, trimethylene (propylene), tetramethylene (n-butylene) and the others.

As used herein, the "alkyleneoxy group" refers to a divalent group in which an oxygen atom is attached to the above-described alkylene group, and specifically includes an alkylene-O— group having one to six carbon atom(s) ($C_{1-6}$), and alkylene-O— group having one to four atom(s) ($C_{1-4}$) is preferable. The alkyleneoxy group may be attached as a substituent onto two different atoms (for example, carbon atom) at the same time, or may be attached as a substituent onto the same atom (for example, carbon atom) to form a spiro ring.

As used herein, examples of the "halogen atom" include fluorine atom, chlorine atom, bromine atom, or iodine atom. Fluorine atom or chlorine atom is particularly preferable.

As used herein, the "haloalkyl group" refers to a straight or branched alkyl group which is substituted with one or three halogen atom(s), and specific examples thereof include difluoromethyl, trifluoromethyl, 1-fluoromethyl, 2-fluoroethyl, and the others.

As used herein, the "haloalkoxy group" refers to an alkyl-O— group substituted with one to three halogen atom(s), and specific examples thereof include trifluoromethoxy and the others.

As used herein, the "hydroxyalkyl group" refers to an alkyl group substituted with one hydroxy group, and specific examples thereof include hydroxymethyl, hydroxyethyl, 2-hydroxy-1,1-dimethylethyl, 4-hydroxy-4-methyl-n-pentyl, and the others.

As used herein, the "alkoxyalkyl group" refers to an alkyl group substituted with one alkoxy group, and specific examples thereof include methoxymethyl, methoxyethyl, 2-methoxy-1,1-dimethylethyl, 4-methoxy-4-methyl-n-pentyl, and the others.

As used herein, the "cycloalkyl group" refers to a monocyclic saturated hydrocarbon group having three to seven carbon atoms ($C_{3-7}$) and adamantyl, and specific examples thereof include cyclopropyl, cyclobutyl, cyclopentyl, cyclohexyl, cycloheptyl, adamantyl, and the others.

As used herein, the "aryl group" refers to six to ten membered aromatic hydrocarbon cyclic group. Monocyclic or bicyclic aryl group is preferable, and specific examples thereof include phenyl, indenyl, and naphthyl, and phenyl is particularly preferable.

As used herein, the "aryl group that may be partially hydrogenated" includes both the above-described aryl group and the above-described aryl group that may be partially hydrogenated, and also include a cyclic group formed by condensation of a phenyl group and a cycloalkyl group, and a cyclic group formed by condensation of a phenyl group and a cycloalkenyl group. Specific examples thereof include phenyl, indenyl, naphthyl, dihydrophenyl, indanyl, dihydronaphthyl, tetrahydronaphthyl, and the others.

As used herein, the "arylalkyl group" refers to an alkyl group in which an alkyl group is substituted with one aryl group, and specific examples thereof include phenylmethyl (benzyl), phenylethyl (phenetyl), phenylpropyl, naphthylmethyl and the others.

As used herein, the "arylalkyloxy group" refers to a monovalent group in which the above-described arylalkyl group is attached to an oxygen atom. Specific examples thereof include phenylmethyloxy (benzyloxy), phenylethyloxy (phenethyloxy), phenylpropyloxy, naphthylmethyloxy and the others.

As used herein, the "heteroaryl group" refers to a 5- to 10-membered monocyclic or bicyclic group containing one to four heteroatom(s) independently selected from the group consisting of sulfur atom, oxygen atom, and nitrogen atom. Preferable examples thereof include a five (5)- to six (6)-membered monocyclic heteroaryl containing at least one nitrogen atoms, and optionally further containing one or more heteroatom(s) independently selected from the group consisting of sulfur atom, oxygen atom, and nitrogen atom. Also another preferable examples thereof include a five (5)- to six (6)-membered monocyclic heteroaryl group containing one to four heteroatom(s) independently selected from the group consisting of oxygen atom, sulfur atom, and nitrogen atom. Specific examples thereof include pyrrolyl, furanyl, thienyl, imidazolyl, pyrazolyl, oxazolyl, isoxazolyl, thiazolyl, tetrazolyl, oxadiazolyl, pyridinyl, pyrazinyl, pyrimidinyl, pyridazinyl, thiazinyl, indolyl, isoindolyl, benzoimidazolyl, and the others.

As used herein, the "aliphatic heterocyclic group" refers to a four (4)- to eight (8)-membered saturated cyclic group containing one to three heteroatom(s) independently selected from the group consisting of oxygen atom, sulfur atom, and nitrogen atom. The aliphatic heterocyclic group may also be a group in which two carbon atoms forming the ring are bridged by an alkylene group to form a bicyclic group or a tricyclic group, and may contain a double bond in the ring. Preferable example thereof includes a four (4)- to seven (7)-membered monocyclic aliphatic heterocyclic group containing at least one nitrogen atoms, and optionally further containing one heteroatom selected from the group consisting of oxygen atom, sulfur atom, and nitrogen atom. Another preferable example includes a five (5)- to six (6)-membered monocyclic aliphatic heterocyclic group containing one or two heteroatom(s) independently selected from the group consisting of oxygen atom, sulfur atom, and nitrogen atom. Specific examples thereof include azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, dihydropyridinyl, homopiperazinyl, homomorpholinyl, 3-azabicyclo[3.1.0]

hexyl, octahydropyrrolo[3,4-c]pyrrolyl, tetrahydrofuranyl, tetrahydropyranyl and the others. Azetidinyl, pyrrolidinyl, piperidinyl, piperazinyl, morpholinyl, thiomorpholinyl, 3-azabicyclo[3.1.0]hexyl, and the others are preferable. Also, pyrrolidinyl, piperidinyl, piperazinyl, morpholinyl, and the others are more preferable, and pyrrolidinyl, piperidinyl, or morpholinyl are particularly preferable. Also, tetrahydrofuranyl, tetrahydropyranyl, piperidinyl, and the others are also preferable.

As used herein, the "aliphatic heterocyclic carbonyl group" refers to a group in which a carbonyl group (C=O) is attached to the above-described aliphatic heterocyclic group, and preferable example thereof includes a four (4)- to seven (7)-membered monocyclic aliphatic heterocyclic group-C(=O)— group containing one to three heteroatom(s) independently selected from the group consisting of sulfur atom, oxygen atom, and nitrogen atom. More preferable example thereof include a four (4)- to seven (7)-membered monocyclic aliphatic heterocyclic carbonyl group containing at least one nitrogen atoms, and optionally further containing one heteroatom selected from the group consisting of sulfur atom, oxygen atom, and nitrogen atom. Particularly preferable example thereof include a five (5)- or six (6)-membered monocyclic aliphatic heterocyclic carbonyl containing at least one nitrogen atoms, in which a carbonyl group is attached to the nitrogen atom in the ring.

As used herein, the "aliphatic heterocyclic sulfonyl group" refers to a group in which a sulfonyl group (O=S=O) is attached to the above-described aliphatic heterocyclic groups, and includes a four (4)- to seven (7)-membered monocyclic aliphatic heterocyclic group-(SO$_2$)— containing one to three heteroatom(s) independently selected from the group consisting of sulfur atom, oxygen atom, and nitrogen atom. A four (4)- to seven (7)-membered monocyclic aliphatic heterocyclic group-(SO$_2$)— containing at least one nitrogen atoms, and optionally further containing one heteroatom selected from the group consisting of sulfur atom, oxygen atom, and nitrogen atom is preferable. In particular, a five (5)- or six (6)-membered monocyclic aliphatic heterocyclic group-(SO$_2$)— containing at least one nitrogen atoms, in which a sulfonyl group is attached to the nitrogen atoms is preferable.

As used herein, the "carbamoyl group" refers to a group represented by —C(=O)NH$_2$.

As used herein, an example of the aryl moiety of the "optionally substituted aryl group" represented by ring A includes a 6- to 10-membered monocyclic or bicyclic aryl, and specific examples thereof include phenyl, naphthyl and the others. A phenyl group is particularly preferable.

An example of the heteroaryl moiety of the "optionally substituted heteroaryl group" represented by ring A includes a five (5)- to six (6)-membered monocyclic heteroaryl containing at least one nitrogen atoms and optionally further containing one to three heteroatom(s) independently selected from the group consisting of oxygen atom, sulfur atom and nitrogen atom. Specific examples thereof include pyrrolyl, furanyl, thienyl, pyridinyl, pyrimidinyl, pyridazinyl, and the others. A pyridinyl group is particularly preferable.

The substituent in the "optionally substituted aryl group" and "an optionally substituted heteroaryl group" represented by ring A may be one to three group(s) each being independently selected, and includes halogen atom, alkyl group, haloalkyl group, cycloalkyl group, alkoxy group, haloalkoxy group, alkyleneoxy group, and the others. Specific examples of the substituent include fluorine atom, chlorine atom, methyl, ethyl, i-propoyl, trifluoromethyl, cyclopropyl, methoxy, ethoxy, trifluoromethoxy, etyleneoxy, and the others.

Examples of the substituent in the "optionally substituted alkyl group", "optionally substituted cycloalkyl group", "optionally substituted aliphatic heterocyclic group", "optionally substituted aryl group that may be partially hydrogenated", "optionally substituted heteroaryl group", and "optionally substituted carbamoyl group" which are represented by $R^5$ may be one to three group(s), preferably one to two group(s), which may be the identical to or different from each other, and examples of the substituent include halogen atom; hydroxyl group; oxo group; cyano group; alkyl group; hydroxyalkyl group; alkoxyalkyl group; haloalkyl group; cycloalkyl group; alkoxy group; alkanoyl group; alkylsulfonyl group; aliphatic heterocyclic group; aliphatic heterocyclic carbonyl group optionally substituted with one to two group(s) independently selected from the group consisting of halogen atom, alkyl group, haloalkyl group, and alkoxyalkyl group; aliphatic heterocyclic sulfonyl group: a carbamoyl group optionally substituted with one to two alkyl group(s); alkyleneoxy group; and the others.

More detailed examples of the substituents include halogen atom; hydroxyl group; oxo group; cyano group; alkyl group; hydroxyalkyl group; alkoxyalkyl group; haloalkyl group; cycloalkyl group; haloalkyl group; cycloalkyl group; alkoxy group; alkanoyl group; alkylsulfonyl group; aliphatic heterocyclic group (wherein the aliphatic heterocyclic group is a four (4)- to seven (7)-membered monocyclic aliphatic heterocyclic group containing one to two heteroatom(s) independently selected from the group consisting of oxygen atom, sulfur atom, and nitrogen atom); aliphatic heterocyclic carbonyl group optionally substituted with one to two group(s) independently selected from the group consisting of halogen atom, alkyl group, haloalkyl group, and alkoxyalkyl group (wherein the aliphatic heterocyclic group is a four (4)- to seven (7)-membered monocyclic aliphatic heterocyclic group containing at least one nitrogen atoms and optionally further one heteroatom selected from the group consisting of oxygen atom, sulfur atom, and nitrogen atom); aliphatic heterocyclic sulfonyl group (wherein the aliphatic heterocyclic group is a four (4)- to seven (7)-membered aliphatic heterocyclic group containing at least one nitrogen atoms and optionally further one heteroatom selected from the group consisting of oxygen atom, sulfur atom, and nitrogen atom); a carbamoyl group optionally substituted with one to two alkyl group(s); alkyleneoxy group; and the others.

As used herein, examples of the "a protecting group for carboxyl group" include an alkyl group optionally substituted with one to three group(s) independently selected from the group consisting of halogen atom, alkoxy group, and arylalkyloxy group; an alkenyl group; an aryl group optionally substituted with one to three group(s) selected from the group consisting of halogen atom, alkyl group, and alkoxy group; and an arylalkyl group optionally substituted with one to three group(s) selected from the group consisting of halogen atom, alkyl group, and alkoxy group. Specific examples of the protecting group include methyl, ethyl, n-propyl, i-propyl, n-butyl, t-butyl, methoxymethyl, benzyloxymethyl, propenyl (ally), phenyl, naphthyl, benzyl, methoxybenzyl, dimethoxybenzyl, and the others.

As used herein, the "alkylsulfonyl group" refers to a group in which a sulfonyl (O=S=O) is attached to the above-described alkyl group, and includes a straight or branched alkyl-(SO$_2$)— having one to six carbon atom(s)

($C_{1-6}$), the alkyl-($SO_2$)— group having one to four carbon atom(s) ($C_{1-4}$) is preferable. Specific examples thereof include methansulfonyl (mesyl), ethansulfonyl, propanesulfonyl, and the others.

As used herein, the "alkyl sulfonyloxy group" refers to a monovalent group in which the above-described alkylsulfonyl group is attached to an oxygen atom, and example thereof include a straight or branched alkylsulfonyl-O— group having one to six carbon atom(s) ($C_{1-6}$), and the alkylsulfonyl-O— group having one to four carbon atom(s) ($C_{1-4}$) is preferable. Specific examples thereof include methansulfonyloxy, ethansulfonyloxy, and propanesulfonyloxy, and the others.

As used herein, specific example of the substituent of the "optionally substituted alkylsulfonyloxy group" includes halogen atom, and fluorine atom or chlorine atom are particularly preferable.

As used herein, the "arylsulfonyl group" refers to a monovalent group in which a sulfonyl (O=S=O) is attached to the above-described aryl group. Specific examples thereof include phenylsulfonyl, naphtylsulfonyl, and the others.

As used herein, the "arylsulfonyloxy group" refers to a monovalent group in which the above-described arylsulfonyl group is attached to an oxygen atom. Specific examples thereof include phenylsulfonyloxy, naphtylsulfonyloxy, and the others.

As used herein, specific examples of the substituent in the "optionally substituted arylsulfonyloxy group" include alkyl group, halogen atom, nitro group, and the others. In particular, an unsubstituted group is preferable, or methyl group is preferable as a substituent.

As used herein, examples of the "malonic acid derivative" include malonic acid diester and the others. Specific examples thereof include malonic acid dialkyl esters such as dimethyl malonate, diethyl malonate, and the others, and dimethyl malonate is particularly preferable.

As used herein, examples of "salt" include inorganic acid salts (such as hydrochloride salt, sulfate salt, phosphate salt, hydrobromide salt, and the others); and organic acid salts (such as acetate, oxalate, malonate, 2-methylmalonate, succinate, fumarate, malenate, malate, tartrate, dibenzoyltartrate, citrate, methanesulfonate, benzenesulfonate, tosylate, and the others). Preferable examples thereof include hydrobromide salt, malonate, 2-methylmalonate, fumarate, and dibenzoyltartrate, and more preferable examples thereof include malonate, 2-methylmalonate, and fumarate. Furthermore preferable examples thereof include 2-methylmalonate and fumarate. Particular preferable example include 2-methylmalonate.

As used herein, the "hydrophobic solvent" refers to a generic solvent which has low water-solubility and is immiscible with water. Examples of the hydrophobic solvent include esters (such as ethyl acetate and isopropyl acetate); halogenated aliphatic hydrocarbons (such as methylene chloride); ethers (such as tetrahydrofuran and t-butyl methyl ether); aromatic hydrocarbons (such as toluene); aliphatic hydrocarbons (such as heptane), and the others. Ethyl acetate, isopropyl acetate, methylene chloride, and aromatic hydrocarbons (such as toluene) are preferable, and toluene is particularly preferable.

As used herein, the "isolation" refers to a procedure in which an usual purification procedure (such as crystallization, recrystallization, and various kinds of chromatography) is performed and thereafter, the resulting products are dried.

As used herein, the "succession of reactions" or "reactions are conducted successively" refers to "the reaction solutions are used as it is in the next step (for example, the second step) without purifying and/or drying the product obtained in a step", "the concentrated reaction solutions are used in the next step", or "the product is used in the next step without drying it after it is obtained as a solid by a crystallization".

As used herein, the "obtained as a crystal" refers to "the product is obtained as a solid (excluding an amorphous) by crystallization", and doesn't include a drying procedure.

As used herein, the "drying" refers to "making an adhered amount of solvent contained in solids (excluding an amorphous) into 2 w/w % or less by heating and/or reducing a pressure. The "without drying" refers to "using the obtained solids (excluding an amorphous) as it is to the next procedure". Here a solvent which is a partial of crystal component (such as a crystal water) is not included as an adhered solvent.

(Embodiment)

The present invention relates to the following processes (1) to (7). The process of the present invention comprises at least one process(es) selected from the processes (1) to (7).

(1) Preparation of the Compound Represented by Formula (V) from the Compound Represented by Formula (III) and the Compound Represented by Formula (VI)

In one embodiment of the process of the present invention, the process comprises that a compound represented by formula (III):

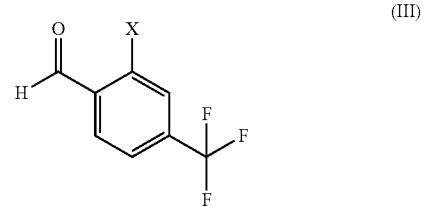

(III)

(wherein X represents a halogen atom, an optionally substituted alkylsulfonyloxy group, or an optionally substituted arylsulfonyloxy group)

is reacted with a compound represented by formula (IV):

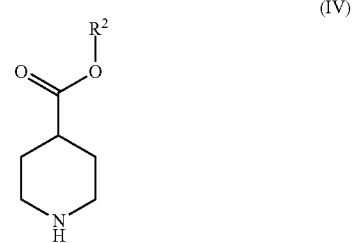

(IV)

(wherein $R^2$ represents a protecting group for carboxy group) or salts thereof to prepare a compound represented by formula (V):

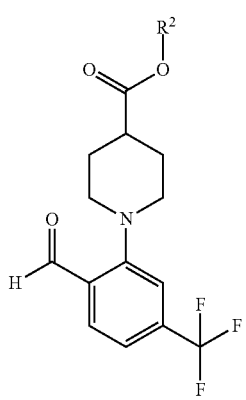

(wherein R² represents a protecting group for carboxy group).

Examples of a protecting group of a carboxyl group represented by R² include an alkyl group optionally substituted with one to three groups independently selected from the group consisting of halogen atom, alkoxy group, and arylalkyloxy group; an alkenyl group; an aryl group optionally substituted with one to three groups independently selected from the group consisting of halogen atom, alkyl group and alkoxy group; or an arylalkyl group optionally substituted with one to three groups independently selected from the group consisting of halogen atom, alkyl group and alkoxy group. An alkyl group optionally substituted with one to three groups independently selected from the group consisting of halogen atom, alkoxy group and arylalkyloxy group is preferable. An alkyl group is more preferable, and methyl, ethyl or t-butyl is further more preferable, and t-butyl is particularly preferable.

The reaction of the compound represented by formula (III) with the compound represented by formula (IV) or salts thereof can be conducted in an appropriate solvent in the presence of a base.

A solvent may be anything that does not disturb the present reaction, and example of an organic solvent includes hydrophobic solvent that is immiscible with water. For examples, aromatic hydrocarbons such as toluene; esters such as butyl acetate and isopropyl acetate; aliphatic hydrocarbons such as n-heptane; halogenated aliphatic hydrocarbons such as dichloroethane; ethers such as dimethoxyethane; or mixed solvents of two or more of these solvents are preferable. Aromatic hydrocarbons such as toluene are particularly preferable. The amount of the solvent is preferably 2 to 20 times as the used amount of the reactants. In the case where the reaction is conducted in a biphasic solvent, the ratio of the organic solvent to water is preferably 1/20 to 10/1.

For examples of the base, alkali metal carbonates such as sodium carbonate, potassium carbonate, cesium carbonate; alkali metal hydrogen carbonates such as sodium hydrogen carbonate and potassium hydrogen carbonate; alkyl hydroxides such as sodium hydroxide and potassium hydroxide; amines such as triethylamine, diisopropylethylamine and 1,8-diazabicyclo[5.4.0]-7-undecene: pyridine, and the others can be used. Alkali metal carbonates such as sodium carbonate and potassium carbonate are preferable.

The used amount of the compound represented by formula (IV) is within a range of 0.2 to 5 times molar equivalent(s), preferably 0.9 to 1.1 times molar equivalent(s), as 1 mole of the compound represented by formula (III). Also, the used amount of the base is within a range of 1 to 4 time(s) molar equivalent(s), as opposed to 1 mole of the compound represented by formula (III).

The reaction proceeds preferably at 60° C. to 120° C., and particularly preferably at 80° C. to 100° C.

The compound represented by formula (V) can be used as a starting material in the next step without isolating it.

(2) Preparation of the compound of formula (VI) from the compound of formula (V)

In one embodiment of the process of the present invention, a compound represented by formula (V) is reacted with a nitromethane to prepare a compound represented by formula (VI):

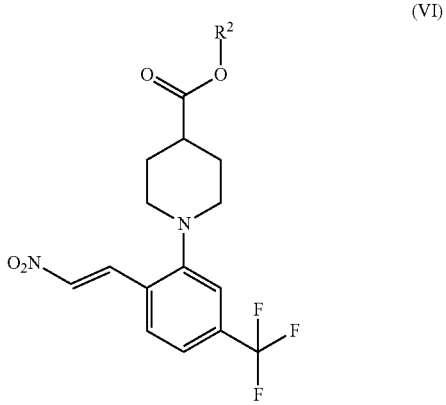

wherein R² represents a protecting group of carboxyl group.

A reaction of a compound represented by formula (V) with nitromethane can be conducted in an appropriate solvent in the presence of a base.

A solvent may be anything that does not disturb the present reaction. However, the compound represented by formula (VI) has some risks of explosion, and the compound is preferably used to the next step without obtaining it as a crystal or drying it, and the present reaction is preferably conducted in the same solvent as the hydrophobic solvent used in the next step. As an example of the solvent, aromatic hydrocarbons such as toluene; esters such as ethyl acetate and isopropyl acetate; aliphatic hydrocarbons such as heptane: halogenated aliphatic hydrocarbons such as methylene chloride; or mixed solvents of two or more of the solvents. Nitromethane can be used as a solvent. The amount of the solvent is preferably 1 to 20 times as the used amount of the reactants.

As an examples of the base, alkali metal alkoxides such as sodium methoxide, sodium ethoxide, potassium t-butoxide; alkylamines such as pyperidine can be used, and alkali metal alkoxides such as sodium methoxide, sodium ethoxide, and potassium t-butoxide are preferable, and sodium methoxide and sodium ethoxide are particularly preferable.

The used amount of nitromethane is, for example, within a range of 1 to 20 times molar equivalent(s), preferably 1 to 10 times molar equivalent(s), as 1 mole of the compound represented by formula (VI). The used amount of the base, is, for example, preferably within a range of 0.01 to 0.2 times molar equivalent(s), more preferably 0.01 to 0.1 times molar equivalent(s), as 1 mole of the compound represented by formula (VI).

The reaction proceeds preferably at −20 to 60° C., particularly preferably at 10 to 35° C.

Also, the present step can be subjected to a dehydration reaction after the reaction of a compound represented by formula (V) with nitromethane as needed. The dehydration reaction can be conducted by reacting with an alkylsulfonyl halides such as methanesulfonyl chloride, an arylsulfonyl halides such as p-toluenesulfonyl chloride, or an alkyl halides such as acetyl chloride in an appropriate solvent in the presence of a base.

As the base, amines such as triethylamine and diisopropylethylamine, and triethylamine can be preferably used. A solvent may be anything that does not disturb the dehydration reaction. However, the compound represented by formula (VI) has some risks of explosion, and thus is preferably used to the next step without obtaining it as a crystal or drying it, and the present reaction is preferably conducted in the same solvent as the hydrophobic solvent used in the next step. As example of the solvent, aromatic hydrocarbons such as toluene; esters such as ethyl acetate and isopropyl acetate; aliphatic hydrocarbons such as heptane; halogenated aliphatic hydrocarbons such as methylene chloride; ethers such as tetrahydrofuran; or mixed solvent of these solvents are preferable. Further, as the solvent for dehydration reaction, the solvent can be used as the same solvent as those used in the reaction of the compound represented by formula (V) with nitromethane. Also, the reaction with nitromethane and the dehydration reaction can be conducted in one-pot approach.

The compound represented by formula (VI) can be used to the next step, without obtaining it as a crystal and/or drying it, as a reaction solution containing the compound represented by formula (VI) as it is, or as a concentrated reaction solution thereof. Here the above-described operation includes the case where any one of or both of obtaining the compound represented by formula (IV) as a crystal and drying it. Also, the present step can be conducted in the hydrophobic solvent as the hydrophobic solvent that is used for the step for reacting the compound represented by formula (VI) with a malonic acid derivative, thereby the successive reactions of these two steps can be conducted.

(3) Preparation of the Compound (VII) from the Compound (VI)

In one embodiment of the process of the present invention, the process comprises a reaction of the compound represented by formula (VI) with a malonic acid derivative in a biphasic solvent of hydrophobic solvent and water, in the presence of a base and an asymmetric catalyst to produce a compound represented by formula (VII):

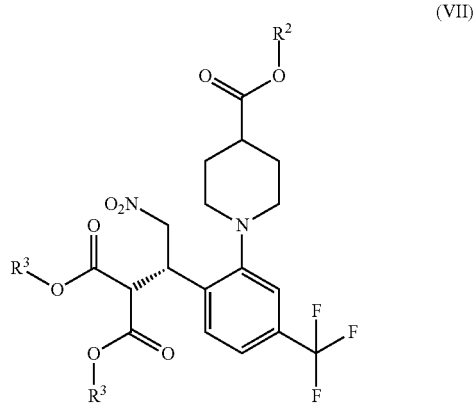

(VII)

[wherein $R^2$ and $R^3$ each independently represents a protecting group of carboxyl group)

This reaction can remove acidic substances which are present in the reaction system effectively out of the reaction system, and can thus promote the proceeding of the reaction and also improve the enantioselectivity of the reaction product. Accordingly, the present reaction is preferably conducted in a biphasic solvent of a hydrophobic solvent and water in the presence of a base. Also, even if water is present in a reaction system, there is no adverse effect on the reaction, and accordingly there is no need to obtain as a crystal the nitrostylene derivative having some risks of explosion (such as the compound represented by formula (VI)), or to dry it, and the process of the present invention is a safe method.

The hydrophobic solvent is a solvent that is immiscible with water, and examples of the solvent include aromatic hydrocarbons such as toluene, aliphatic hydrocarbons such as ethyl acetate and isopropyl acetate; halogenated aliphatic hydrocarbons such as methylene chloride; or mixed solvents of two or more of the solvents. The used amount of the solvent is preferably 1 to 10 time(s) as the used amount of the reactants, or 0.1 to 3 times as the used amount of water.

As the base, alkali metal carbonates such as sodium carbonate, potassium carbonate and cesium carbonate; alkali metal hydrogen carbonates such as sodium hydrogen carbonate, potassium hydrogen carbonate can be used. Alkali metal hydrogen carbonates such as sodium hydrogen carbonate and potassium hydrogen carbonate are preferable, and sodium hydrogen carbonate is particularly preferable.

The asymmetric catalyst may be a substance which can provide a compound having a desired stereo configuration selectively, and examples thereof include 1-[3,5-bis(trifluoromethyl)phenyl]-3-[(1R,2R)-(−)-2-(dimethylamino)cyclohexyl]thiourea, and 6'-hydroxy quinine and the others, which are limited thereto. The used amount of the catalyst is within a range of 0.1 to 30 molar equivalent(s) %, preferably 1 to 5 molar equivalent(s) %, as opposed to 1 mole of the compound represented by formula (VI).

Examples of the malonic acid derivatives include malonic acid diester represented by formula $CH_2(CO_2R^3)_2$ (wherein the symbols are the same as defined above) (such as dimethyl malonate).

The used amount of the malonic acid derivative is within a range of 1 to 5 time (s) molar equivalent(s), preferably within a range of 1 to 2 time(s) molar equivalent(s), as 1 mole of the compound represented by formula (VI).

The present reaction proceeds preferably at 0 to 40° C., particularly preferably at 10 to 30° C.

The compound represented by formula (VII) can be used as a solution containing the same as it is, to the next step without obtaining as a crystal, however, the compound obtained as a crystal can be used to the next step so that the yields in the next step and the steps that follows the next step can be largely improved. Even in the case where the compound is obtained as a crystal, the compound may be used to the next step without drying it.

Examples of a protecting group of a carboxyl group represented by $R^2$ include an alkyl group optionally substituted with one to three groups independently selected from the group consisting of halogen atom, alkoxy group and arylalkyloxy group; an alkenyl group; an aryl group optionally substituted with one to three groups independently selected from the group consisting of halogen atom, alkyl group and alkoxy group; or an arylalkyl group optionally substituted with one to three groups independently selected from the group consisting of halogen atom, alkyl group and alkoxy group. An alkyl group optionally substituted with one to three groups independently selected from the group consisting of halogen atom, alkoxy group and arylalkyloxy group is preferable. An alkyl group is more preferable, and methyl, ethyl or t-butyl is more preferable, and t-butyl is particularly preferable.

Examples of a protecting group of carboxyl group represented by $R^3$ include an alkyl group optionally substituted with one to three groups independently selected from the group consisting of halogen atom, alkoxy group, and arylalkyloxy group; an alkenyl group; an aryl group optionally substituted with one to three groups independently selected from the group consisting of halogen atom, alkyl group and alkoxy group; or an arylalkyl group optionally substituted with one to three groups independently selected from the group consisting of halogen atom, alkyl group and alkoxy group. An alkyl group optionally substituted with one to three groups independently selected from the group consisting of halogen atom, alkoxy group, and arylalkyloxy group is preferable. An alkyl group is more preferable, and methyl or ethyl is further more preferable, and methyl is particularly preferable.

The protecting group of carboxyl group represented by $R^2$ and the protecting group of carboxyl group represented by $R^3$ may be selected as the same protecting group, however, a different protecting group is preferably selected.

(4) Preparation of the Compound of Formula (VIII) from the Compound of Formula (VII)

In one embodiment of the process of the present invention, the process comprises that a compound represented by formula (VII) is subjected to a reduction reaction and a ring closure reaction to prepare a compound represented by formula (VIII):

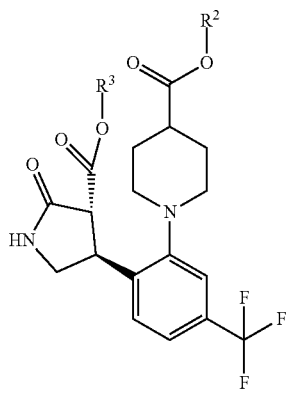

(VIII)

(wherein $R^2$ and $R^3$ each independently represents a protecting group of carboxyl group). The reduction reaction and the ring closure reaction may be successive reactions.

The reduction reaction is preferably conducted in a solvent, and the solvent may be anything that does not disturb the present reaction, and example of the solvent include alcohols such as methanol, ethanol, and isopropanol; halogenated aliphatic hydrocarbons such as methylene chloride; ethers such as tetrahydrofuran and dimethoxyethane; aromatic hydrocarbons such as toluene; esters such as ethyl acetate; or mixed solvents of two or more of the solvents; or mixed solvents with water. Methanol and dimethoxyethane are preferably included. The used amount of the solvents is within a range of 5 to 20 times as the used amount of the reactants.

Examples of the reducing agent include a combination of hydrogen sources (such as hydrogen gas, formic acid, or ammonium formate) and palladium catalysts (such as palladium catalyst supported on activated carbon), a combination of hydrogen sources (such as hydrogen gas, formic acid, or ammonium formate) and rhodium catalysts (such as rhodium catalyst supported on activated carbon), a combination of sodium borohydride and nickel chloride, a combination of hydrochloric acid and metal (such as iron, zinc, thin, thin chloride). The present reaction proceeds preferably by using a reduction via a catalytic hydrogenation, and as the reducing agent, a combination of hydrogen gas and palladium catalyst, or a combination of hydrogen gas and rhodium catalyst is preferable. A combination of hydrogen gas and rhodium catalyst is particularly preferably used. The used amount of the hydrogenated catalyst is within a range of 1 to 50% by weight, particularly preferably within a range of 3 to 40% by weight, as opposed to 1 mole of the compound represented by formula (VII).

Also, when the present process step is conducted via a hydrogenation, the reaction is conducted under ordinary pressure to medium pressure. Specifically, the reaction is conducted under 1 bar to 10 bar, more preferably 3 bar to 8 bar.

In the present reaction, an acid may be added to promote a reduction reaction. Examples of the acid include hydrochloric acid and acetic acid. Next, if desired, a cyclization reaction can be conducted. In order to promote the cyclization reaction, a base may be added. Example of the base includes 1,8-diazabicyclo[5.4.0]-7-undecene, and triethylamine.

(5) Preparation of the Compound of Formula (IX) from the Compound of Formula (VIII)

In one embodiment for the process of the present invention, the process comprises that a compound represented by formula (VIII) is subjected to a reduction reaction to prepare a compound represented by formula (IX):

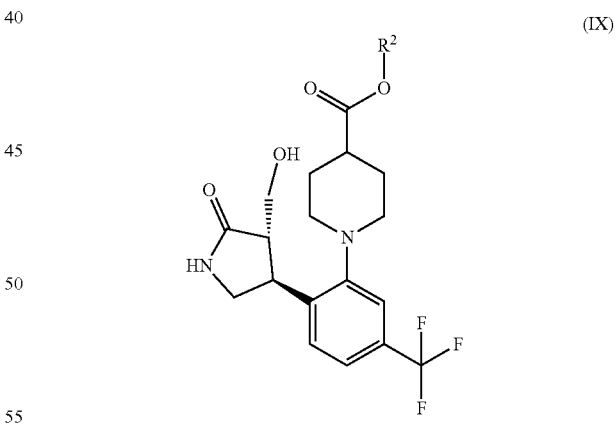

(IX)

(wherein $R^2$ represents a protecting group of carboxyl group).

The reduction reaction of a compound represented by formula (VIII) can be conducted in an appropriate solvent in the presence of a reducing agent according to a usual method.

The solvent may be any solvent that does not disturb the present reaction, however, more preferably, if the solvent is selected as the same solvent as the above-described solvent used in the step for obtaining the compound represented by formula (VIII), the total two steps comprising the present step together with the above-described pre-step can be conducted successively. Specific examples of the solvent include alcohols such as methanol, ethanol and isopropanol; ethers such as dimethoxyethane and tetrahydrofuran, or mixed solvents thereof, and dimethoxyethane is preferable. The used amount of the solvent is preferably within a range of 3 to 10 times as the used amount of the reactants.

Examples of the reducing agent include borohydrides such as sodium borohydride; and aluminium hydrides such as diisobutylalunimium hydrides. The used amount of the reducing agent is within a range of 0.5 to 3 times molar equivalent(s), particularly preferably within a range of 1 to 2 time(s) molar equivalent(s), as 1 mole of the compound represented by formula (VIII).

As aforementioned, the total three steps for preparing a compound represented by formula (VII) from the compound represented by formula (III) can be conducted successively, and also the total two steps for preparing a compound represented by formula (IX) from a compound represented by formula (VII) can be conducted successively by using the same solvents, and further the compound represented by formula (VII) is not needed to isolate, and the total five steps can be thus conducted successively. Preferably the compound represented by formula (VII) is obtained as a crystal, and which is then applied to the next step, however, in the other steps, the reaction solution containing the reaction products can be used as it is, or the reaction solution after the concentration can be used, to the next step. Even in the case where the compound represented by formula (VII) is obtained as a crystal, the drying procedure is not needed.

The reaction for preparing the compound represented by formula (VII) from the compound represented by formula (VI) is preferably conducted in a biphasic solvent of hydrophobic solvent and water. The reaction of the compound represented by formula (III) with the compound represented by formula (IV) is also preferably conducted in a biphasic solvent of hydrophobic solvent and water.

(6) Preparation of a Compound of Formula (II) from a Compound of Formula (IX)

In one embodiment of the process of the present invention, the process comprises that in a compound represented by formula (IX), a hydroxy group in the formula (IX) is converted into an appropriate substituent $R^1$ according to a known method in an organic chemistry, if desired, followed by making the compound into salts thereof to prepare a compound represented by formula (II):

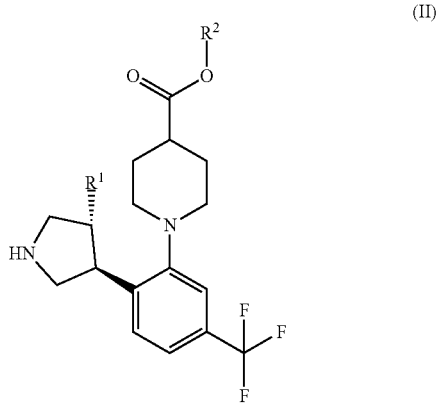

(II)

(wherein $R^1$ represents an alkyl group optionally substituted with one or more groups independently selected from the group consisting of halogen atom, hydroxy group, cyano group and alkoxy group (such as methyl), and $R^2$ represents a protecting group of carboxyl group) or salts thereof.

Examples of "salt (s)" of the compound represented by formula (II) include inorganic acid salts such as hydrochloride salt, sulfate, phosphate, and hydrobromide salt; and organic acid salts such as acetate, oxalate, malonate, 2-methylmalonate, succinate, fumarate, malenate, malate, tartrate, dibenzolyl tartrate, citrate, methanesulfonate, benzenesulfonate, and tosylate. Hydrobromide, malonate, 2-methylmalonate, fumarate, and dibenzoyl tartrate are preferably included, and malonate, 2-methylmalonate and fumarate are more preferably included. 2-Methyl malonate and fumarate are further more preferably included. 2-Methyl malonate is particularly preferably included.

In one embodiment of the present invention, salts of the compound represented by formula (II) is preferably a compound represented by the following formula (XI):

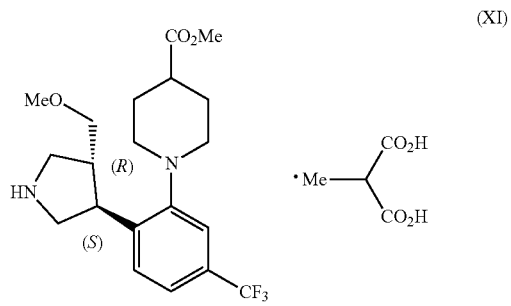

(XI)

The method for converting a compound represented by formula (IX) into a compound represented by formula (II) can be conducted, for example, according to a method described in the above-described Patent document 1 and the like. Specifically, according to a usual method, a reduction reaction is conducted, or a hydroxyl group can be converted by halogenation, alkylation, cyanation, and the like. As needed, a functional group may be protected or deprotected.

The halogenation of a hydroxy group is conducted, for example, by reacting with a halogenating agent in a solvent. A solvent may be anything that does not disturb the present reaction. Examples of the halogenating agent include (diethylamino) sulfate fluoride, thionyl chloride, phosphorus tribromide, hydrogen iodide, N-chlorosuccinimide, and N-bromosuccinimide and the like. In order to promote the reaction, triphenylphosphine, triethylamine, or pyridine and the like may be co-existed. The hydroxy group may be reacted with a sulfonylating agent such as methanesulfonyl chloride and p-toluenesulfonyl chloride, followed by reacting with a halogenated agent such as sodium iodide, potassium iodide, sodium bromide, and sodium chloride.

The alkylation of a hydroxyl group is conducted, for example, by reacting with an alkylating agent in a solvent in the presence of a base. A solvent may be anything that does not disturb the present reaction. Examples of the alkylating agent include alkyl halides such as methyl iodide, methyl bromide, and ethyl bromide; methyl trifluoromethanesulfonate, and Meerwein reagent. Examples of the base include alkali metal carbonates such as sodium carbonate, potassium carbonate and cesium carbonate; alkali metal hydroxides such as sodium hydroxide, potassium hydroxide, and lithium hydroxides; alkali metal hydrides such as sodium hydride; and alkali alkoxides such as potassium t-butoxide. An alkali metal hydroxides such as sodium hydroxide, potassium hydroxide, and lithium hydroxide are preferable, and sodium hydroxide is particularly preferable.

A cyanation of a hydroxy group is conducted, for example, by reacting with a cyanating agent in a solvent. A solvent may be anything that does not disturb the present reaction. Examples of the cyanating agent include acetone cyanohydrin and the like. The hydroxy group may be reacted with a sulfonylating agent such as methanesulfonyl chloride and p-toluenesulfonyl chloride, followed by reacting with a cyanating agent such as sodium cyanide. In order to promote the reaction, a base such as triethylamine may be co-existed.

(7) Preparation of a Compound of Formula (I) from a Compound of Formula (II)

In one embodiment of the process of the present invention, the process comprises that the compound represented by formula (II) or salts thereof is reacted with a compound represented by formula (X):

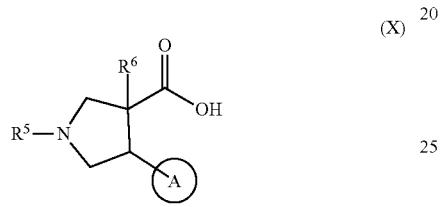

(wherein the cycle A represents an optionally substituted aryl group, or an optionally substituted heteroaryl group, $R^5$ represents an optionally substituted alkyl group, an optionally substituted cycloalkyl group, an optionally substituted aliphatic heterocyclic group, an optionally substituted aryl group that may be partially hydrogenated, an optionally substituted heteroaryl group, an optionally substituted carbamoyl group, or a hydrogen atom, and $R^6$ represents a halogen atom, an alkyl group, or an optionally substituted alkoxy group)

or salts thereof on the nitrogen atom of a pyrrolidine group in the formula (II) according to a known method in an organic chemistry field, further, if desired, followed by making the resulting compound into pharmaceutically acceptable salts thereof to prepare a compound represented by formula (I):

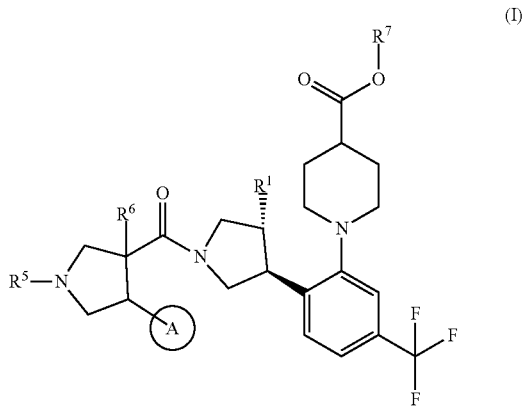

(wherein the ring A, $R^5$, and $R^6$ are the same as defined above, $R^1$ represents an alkyl group optionally substituted with one or more groups independently selected from the group consisting of halogen atom, hydroxyl group, cyano group, and alkoxy group (such as methyl, methoxymethyl), and $R^7$ represents a hydrogen atom, or a protecting group of a carboxyl group)

or pharmaceutically acceptable salts thereof.

In one embodiment of the present invention, $R^1$ in the formula (I) is preferably methoxymethyl.

In one embodiment of the present invention, the salts of the compound represented by formula (II) is preferably salts of the above-described compound represented by formula (XI).

The method for converting a compound represented by formula (II) into the compound represented by formula (I) can be conducted, for example, according to a method described in the above-described patent document 1. Specifically, the compound represented by formula (II) is subjected to an amidation with a compound represented by formula (X):

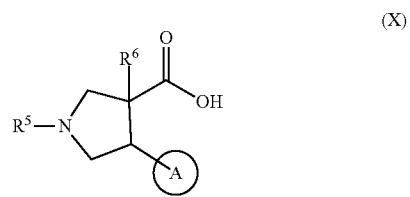

(wherein the symbols are the same as defined above), as needed, followed by a protection or a deprotection of a functional group in the resulting compound to prepare a compound represented by formula (I).

Examples of the ring A include an aryl group optionally substituted with one to three groups independently selected from the group consisting of halogen atom, alkyl group, haloalkyl group, cycloalkyl group. alkoxy group, haloalkoxy group, and alkyleneoxy group; and a heteroaryl group optionally substituted with one to two groups independently selected from the group consisting of halogen atom and alkoxy group. Preferred examples of the ring A include an aryl group optionally substituted with one to two groups independently selected from the group consisting of halogen atom, alkyl group, haloalkyl group, cycloalkyl group, alkoxy group, haloalkoxy group, and alkyleneoxy group; and a heteroaryl group optionally substituted with halogen atom or alkoxy group. More preferred example of the ring A includes an aryl group optionally substituted with one to two groups independently selected from the group consisting of halogen atom, alkyl group, haloalkyl group, cycloalkyl group, alkoxy group, haloalkoxy group, and alkyleneoxy group, and particularly preferred example of the ring A includes an aryl group optionally substituted with alkoxy group.

As $R^5$ group, an alkyl group, an optionally substituted cycloalkyl group, an aliphatic heterocyclic group, or an optionally substituted heterocyclic group is preferable. In more detail, an alkyl group; a cycloalkyl group optionally substituted with cyano group or alkoxy group; a five- to six-membered monocyclic aliphatic heterocyclic group containing one to two heteroatoms independently selected from the group consisting of oxygen atom, sulfur atom and nitrogen atom; or a heteroaryl group optionally substituted with alkyl group (wherein the heteroaryl group represents a five- to six-membered monocyclic heteroaryl group containing one to four heteroatoms independently selected from the group consisting of oxygen atom, sulfur atom and nitrogen atom) are preferable. Specifically, a t-butyl group; a cyclopentyl group; a cyclohexyl group optionally substituted with methoxy group, ethoxy group or cyano group; a tetrahydropyranyl group; or a pyridyl group optionally substituted with methyl group are preferable.

As $R^6$ group, preferred examples thereof include a halogen atom, an alkyl group, and alkoxy group and the like, and a halogen atom or an alkoxy group is more preferable. A fluorine atom or a methoxy group is particularly preferable.

As $R^7$ group, a hydrogen atom; an alkyl group optionally substituted with one to three groups independently selected from the group consisting of halogen atom, alkyl group and arylalkyloxy group; an alkenyl group; an aryl group optionally substituted with one to three groups independently selected from the group consisting of halogen atom, alkyl group and alkoxy group; or an arylalkyl group optionally substituted with one to three groups independently selected from the group consisting of halogen atom, alkyl group and alkoxy group is included. A hydrogen atom; or an alkyl group optionally substituted with one to three groups independently selected from the group consisting of halogen atom, alkoxy group and arylalkyloxy group is preferable. A hydrogen atom or an alkyl group is more preferable, and a hydrogen atom, a methyl group, an ethyl group or a t-butyl group is more preferable, and a hydrogen atom is particularly preferable.

In one embodiment, salts of the compound represented by formula (II) is the above-described compound of formula (XI).

In one embodiment, $R^1$ in the formula (I) is preferably a methoxymethyl.

A compound represented by formula (I) or pharmaceutically salts thereof are described in the above-described patent document 1, and has a melanocortin receptor agonist activity, and is thus a useful compound for preventing or treating various diseases or symptoms in which an activation of melanocortin receptor is involved.

All compounds that are obtained in each step in the present invention can be obtained as a salt thereof.

As used herein, examples of "pharmaceutically acceptable salt" include inorganic acid salts such as hydrochloride salt, sulfate, phosphate, and hydrobromide salt; and organic acid salts such as acetate, fumarate, oxalate, citrate, methanesulfonate, benzenesulfonate, tosylate, and maleate.

EXAMPLES

Hereinafter, the present invention is explained in more detail by using the following Examples and the like, however, the present invention should not be limited to these examples.

Example 1

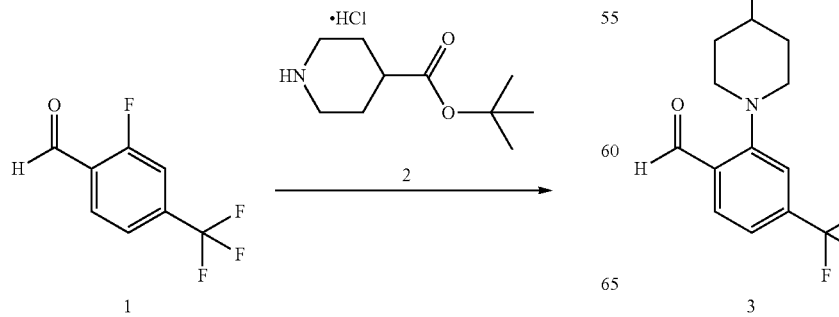

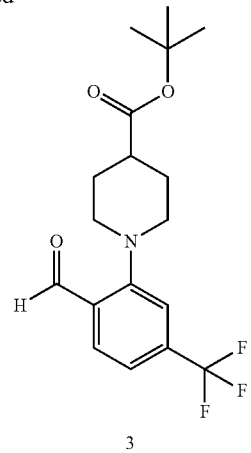

Potassium carbonate (26.1 kg) was dissolved into water (101.5 L), and thereto were added the compound 2 (18.4 kg), toluene (75.2 kg) and the compound 1 (14.8 kg) successively at room temperature, and the reaction mixture was stirred at 85° C. for 22 hours. After the mixture was cooled to 40° C., the organic layers were separately collected, and thereto were added water (101.5 L) and citric acid monohydrate (14.5 kg) at room temperature, and the mixture was stirred. To the separately collected organic layers was added water (101.5 L) at room temperature, and the mixture was stirred, and the separately collected organic layers were concentrated at 50° C. to 60 L. To the concentrated residue was added toluene (47.7 kg), and the mixture was concentrated at 50° C. to 30 L to obtain the solution of the compound 3.

Example 2

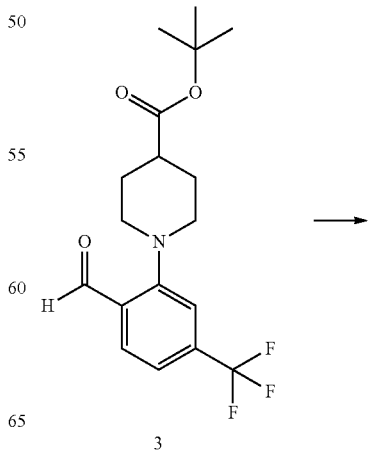

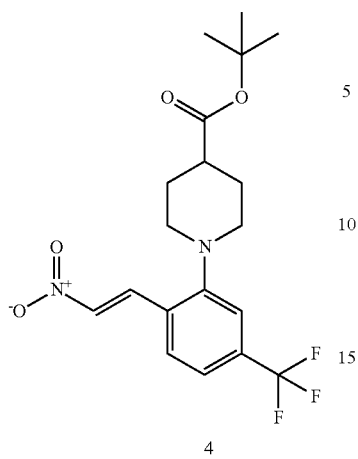

4

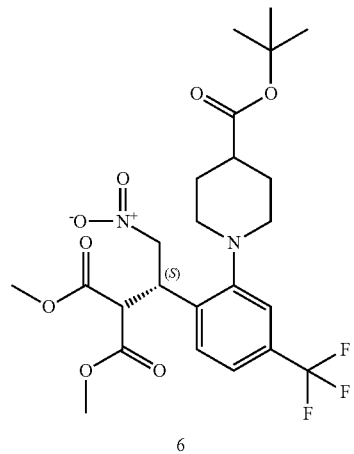

6

To the solution of the compound 3 that was obtained in the Example 1 were added nitromethane (47.0 kg), toluene (12.8 kg), and 28% solution of sodium methoxide in methanol (0.45 kg) successively, and the mixture was stirred for 4 hours. The mixture was cooled to −5° C., and thereto were added toluene (102.3 kg), methanesulfonyl chloride (13.2 kg) and triethylamine (17.1 kg) successively, and the mixture was stirred for 1 hour. Thereto was added water (29.7 L) at room temperature, and the mixture was stirred, and the separately collected organic layers were concentrated at 50° C. to 120 L. To the concentrated residue was added toluene (79.5 kg), and the mixture was concentrated at 50° C. to 120 L. To the concentrated residue was added toluene (77.0 kg) again, and the mixture was concentrated at 50° C. to 120 L to obtain the solution of the compound 4.

Example 3

To the solution of the compound 4 that was obtained in the Example 2 were added water (29.6 L), sodium hydrogen carbonate (2.96 kg), diethyl malonate (17.3 kg) and the compound 5 (0.95 kg) successively, and the reaction mixture was stirred for 19 hours. The organic layers were separately collected at 45° C., and concentrated at 50° C. to 60 L. To the concentrated residue was added 2-propanol (92.7 kg), and the mixture was concentrated at 65° C. to 90 L. To the concentrated residue was added 2-propanol (93.5 kg) again, and the mixture was concentrated at 65° C. to 90 L. The mixture was cooled to 25° C. and then stirred for 16 hours. The mixture was further cooled to −9° C. and then stirred for 2 hours, and the crude crystals were collected by filtration, and washed with water (147.8 L). The crude crystals were dissolved in 1,2-dimethoxyethane (106.3 kg) at room temperature, and the mixture was concentrated at 50° C. to 50 L. To the concentrated residue was added 1,2-dimethoxyethane (107.0 kg), and the mixture was concentrated at 50° C. to 50 L. To the concentrated residue was added 1,2-dimethoxyethane (106.2 kg) again, and the mixture was concentrated at 50° C. to 50 L to obtain a solution of the compound 6.

Example 4

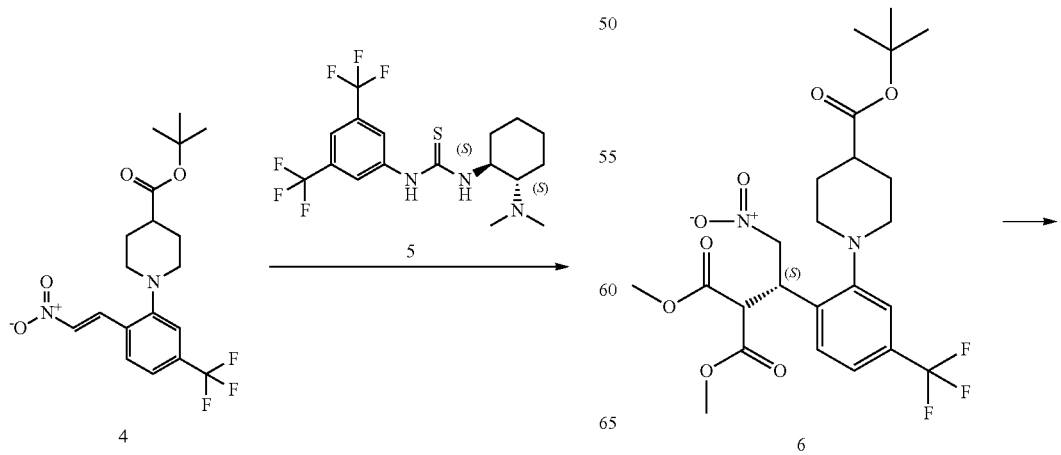

-continued

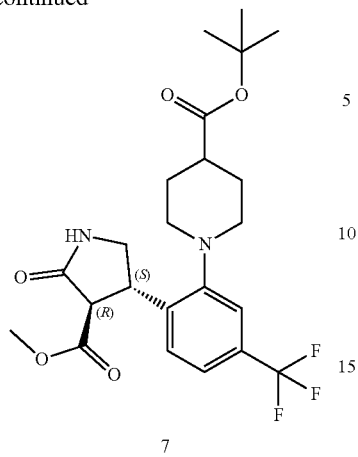

7

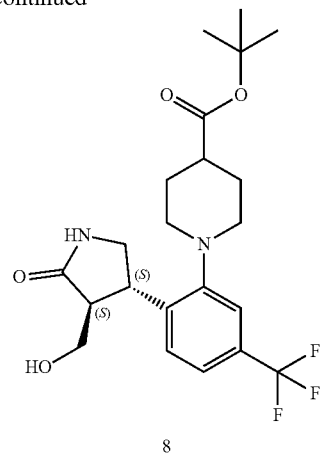

8

To the solution of the compound 6 that was obtained in the Example 3 were added 1,2-dimethoxyethane (91.6 kg), 5% rhodium-carbon (moisture 56.3%, 10.6 kg), and acetic acid (2.99 kg) successively, and the reaction mixture was pressurized (0.6 MPa) with hydrogen at 60° C., and stirred for 20 hours. After the mixture was cooled to 25° C., the solids in the reaction mixture were filtered to obtain the filtrates. The filtered residue was washed with 1,2-diethoxyethane (114.8 kg), and the wash solutions were combined with filtrates, and the combined mixture were concentrated at 50° C. to 60 L. To the concentrated residue was added 1,2-dimethoyethane (115.0 kg), and the mixture was concentrated at 50° C. to 53 L. To the concentrated residue was added 1,2-dimethoxyethane (114.9 kg) again, and the mixture was concentrated at 50° C. to 53 L. The concentrated residue was cooled to room temperature, and thereto was added 1,2-dimethoxyethane (11.5 kg) to obtain the concentrated solution of the compound 7. A concentrated solution of the compound 7 (1.0 time scale) that was prepared similarly by the above-described procedures, and these concentrated solutions of the compound 7 were combined, and thereto was added 1,2-dimethoxyethane (69.1 kg). The mixture was concentrated at 50° C. to 110 L, and thereto were added methanol (6.76 kg) and 1,2-dimethoxyethane (48.8 kg) successively at room temperature to obtain a solution of the compound 7.

To a suspension of sodium borohydride (7.99 kg) in 1,2-dimethoxyethane (146.7 kg) were added the solution of the compound 7 that was obtained in the Example 4, and 1,2-dimethoxyethane (49.1 kg) successively at 45° C., and then the reaction mixture was stirred for 1 hour and cooled to room temperature. To a solution of ammonium chloride (45.2 kg) in water (169.0 kg) were added the above reaction solutions and 1,2-dimethoxyethane (25.0 kg) successively at 25° C. Thereto was added ethyl acetate (235.7 kg) at room temperature, and the mixture was stirred. The organic layers were separately collected, and thereto was added water (112.3 L) at room temperature, and the separately collected organic layers were concentrated at 50° C. to 170 L. To the concentrated residue was added ethyl acetate (253.7 kg), and the mixture was concentrated at 50° C. to 170 L. Thereto was added heptane (231.5 kg) at 50° C., and the mixture was stirred for 0.7 hours, and cooled to 10° C., and stirred for 15 hours. The crystals were collected by filtration, and the crystals were washed with a mixed solution of ethyl acetate (25.6 kg) and heptane (58.0 kg) that was cooled to 10° C., and further washed with water (112.4 L) at room temperature. The crystals were dried at 50° C. to obtain the compound 8 (30.2 kg) (yield 44% based on the compound (1)). MS (ESI) m/z 443 [M+H]+

Example 5

Example 6

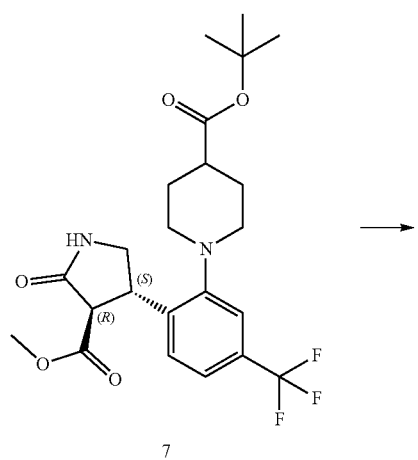

7

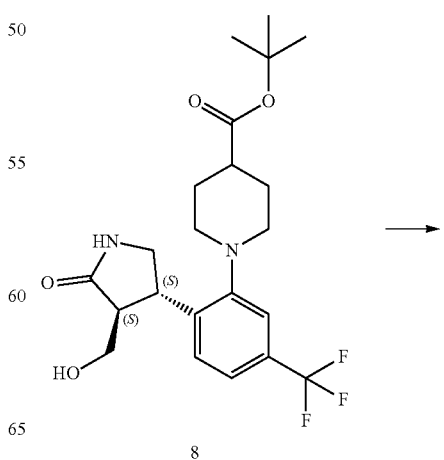

8

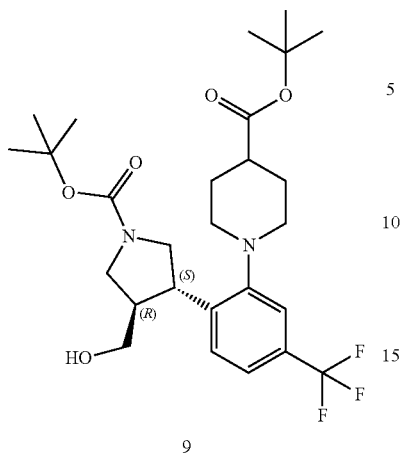

9

To a solution of the compound 8 (29.0 kg) in 1,2-dimethoxyethane (163.6 kg) was added a solution of methyl trifluoromethanesulfonate (16.1 kg) in 1,2-dimethoxyethane (87.9 kg) at 10° C., and the reaction mixture was stirred for 2 hours. To the reaction mixture was added sodium tetrahydroborate (2.5 kg) at 0° C., and the mixture was then stirred at 10° C. for 2 hours. Thereto was added triethylamine (16.6 kg), followed by addition of a solution of di-tert-butyl dicarbonate (13.6 kg) in 1,2-dimethoxyethane (25.0 kg), and the mixture was stirred for 2 hours. The mixture was stirred for additional 2 hours at 45° C., and then cooled to 25° C. Thereto was added toluene (175.7 kg), and the organic layers were separately collected, and thereto was added a solution of ammonium chloride (20.3 kg) in water (182.7 L), and the organic layers were separately collected. The organic layers were then washed with a solution of sodium hydrogen carbonate (5.8 kg) in water (110.2 L), and concentrated to 104 L to obtain a solution of the compound 9.

Example 7

To a suspension of N,N-dimethylformamide (97.9 kg), sodium hydroxide (15.7 kg), toluene (18.0 kg) were added iodomethane (37.2 kg), N,N-dimethylformamide (13.1 kg), and the solution of the compound 9 that was obtained in the Example 6 successively at −10° C., and the reaction mixture was stirred at 0° C. for 10 hours. Thereto were added water (117.6 L), triethylamine (26.5 kg), and toluene (90.0 kg) successively, and the organic layers were separately collected. The organic layers were washed with a solution of ammonium chloride (41.5 kg) in water (373.7 L) twice, and a solution of sodium hydrogen carbonate (10.4 kg) in water (197.2 L) to obtain a solution of the compound 10.

Example 8

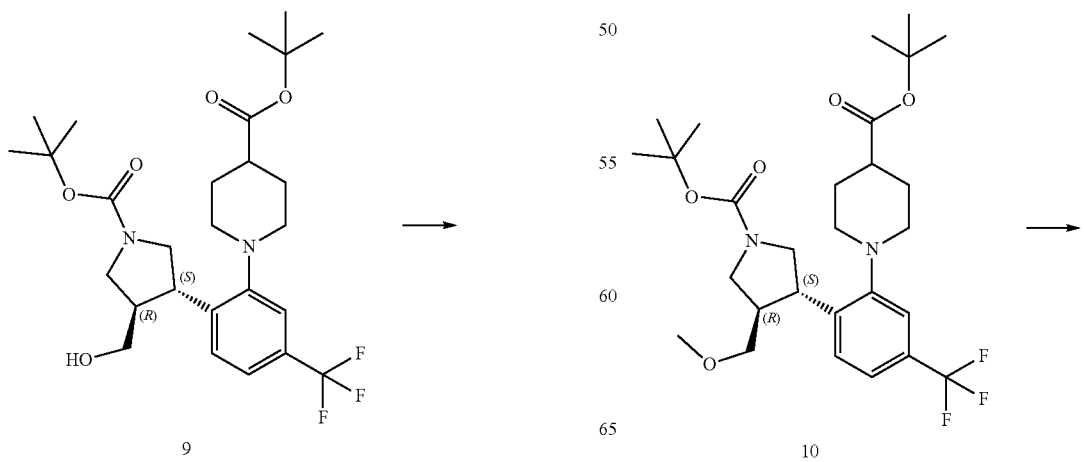

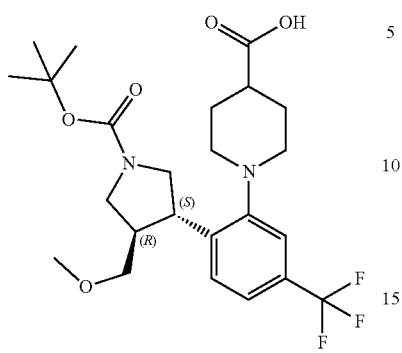

11

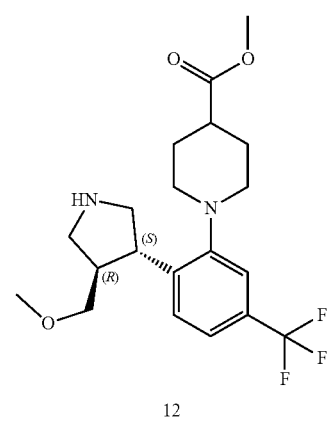

12

To the solution of the compound 10 that was obtained in the Example 7 was added a solution of potassium hydroxide (17.3 kg) in methanol (213.6 L) at 40° C., and the reaction mixture was stirred at 65° C. for 18 hours. The mixture was cooled to 50° C., and thereto were added water (106.8 L) and heptane (121.8 kg), and the aqueous layers were then separately collected. Thereto were added a solution of methanol (10.7 L) in water (7.1 L) and toluene (110.4 kg) successively. Thereto was added a solution of concentrated hydrochloric acid (39.8 kg) in water (159.7 L) at 10° C., and the mixture was stirred, and the organic layers were then separately collected to obtain a solution of the compound 11.

The partial of solution of the compound 11 that was synthesized by the above-described process was purified by silica gel column chromatography (chloroform:methanol=100:0 to 93:7). The resulting residue 80 mg was dissolved into acetone (320 ul), and the mixture was stirred at room temperature, and the precipitated out crystals were collected by filtration, and dried under reduced pressure to obtain the compound 11 (36 mg). MS(ESI) m/z 487 [M+H]+

Example 9

To methanol (127.6 L) was added acetyl chloride (41.2 kg) at −10° C., and thereto were added dropwise the solution of the compound 11 that was obtained in the Example 8 and methanol (16.0 L) at 15° C., and the reaction mixture was stirred at 20° C. for 4 hours, and thereto was added methanol (16.0 L). Thereto were added an aqueous solution of 24% sodium hydroxide (80.9 kg), water (129.8 L), and a solution of sodium carbonate (13.9 kg) in water (127.7 L) successively at 10° C., and the mixture was mixed while stirring, and the organic layers were separately collected. The organic layers were washed with a solution of sodium chloride (9.6 kg) in water (95.7 L) to obtain a solution of the compound 12.

Example 10

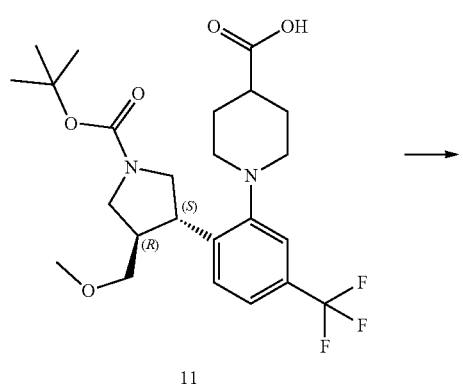

11

12

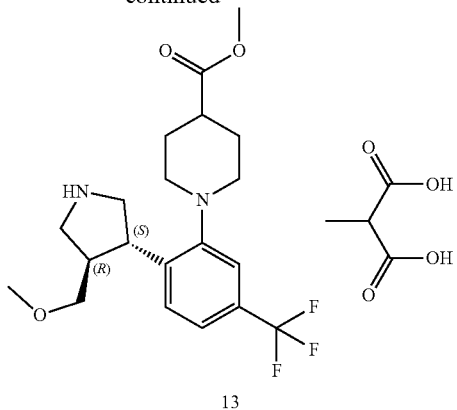

13

To the solution of the compound 12 that was obtained by the Example 9 were added toluene (55.2 kg), ethanol (75.6 kg), and 2-methyl malonic acid (4.9 kg), and the reaction mixture was stirred at 15 to 8° C. for 8 hours. The crystals were collected by filtration, washed with a solution of ethanol (12.4 kg) in toluene (27.8 kg) that was cooled to 8° C., and dried at 50° C. to obtain the compound 13 (15.3 kg) (yields 45% based on the compound (8)). MS (ESI): m/z 401 [M+H]+

The compound 12 as a free product was in the oily form, and thus showed low stability. On the other hand, when the compound 12 was made into a salt form thereof, the stability thereof was improved. In particular, each of malonate salt, 2-methyl malonate, or fumarate of the compound 12 was showed good stability.

The test results of the stability of the compound 13 as 2-methylmalonate salt thereof is described below.

Example 11

[Thermal Stability of Compound 13]

The HPLC of the compound 13 that was obtained in the Example 10 was measured under the below-mentioned condition to confirm 99.0 area % as a purity (column: YMC-Triart C18 (4.6×150 mm, 5 μm), column temperature: 40° C., mobile phase A: water/acetonitrile/trifluoroacetic acid=800/200/0.5, mobile phase B: acetonitrile/trifluoroacetic acid=1000/0.5, gradient program (B %): 30-90% (0-17 min), 90% (17-22 min), 90-30% (22-22.5 min), 30% (22.5-30 min), flow rate: 1.0 mL/min, diluted solution: 50% acetonitrile-water, detector: UV 215 nm).

The compound 13 (1.9 mg) was placed in a brown glass micro tube, and the tube was sealed. The tube was allowed to stand for 7 days in a fan dryer that was set up to 60° C., and then cooled to room temperature. The compounds contained in the micro tube was dissolved by using the diluted solution to make 5 mL, and the HPLC of the diluted solution was measured under the same condition as the measured condition at the timing before standing for 7 days. The purity of the compound 13 was confirmed to be 99.2 area %.

INDUSTRIAL APPLICABILITY

The process of the present invention is useful as a process for preparing an optically active pyrrolidine compound which is useful as an intermediate compound for drug substance, or synthetic intermediate compound thereof.

The invention claimed is:
1. A salt represented by formula (XI):

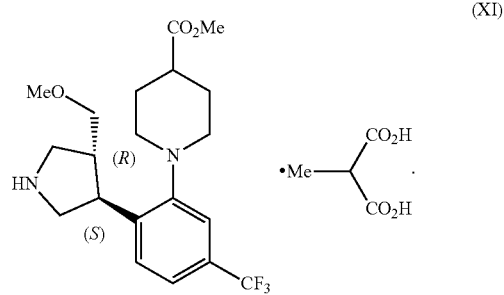

* * * * *